(12) United States Patent
Hamada et al.

(10) Patent No.: US 7,922,822 B2
(45) Date of Patent: Apr. 12, 2011

(54) METHOD FOR CLEANING AND STERILIZING ENDOSCOPIC CAMERA

(75) Inventors: Masahisa Hamada, Tokorozawa (JP); Takehisa Nakayama, Saitama (JP); Kazuko Ichimiya, Tokyo (JP)

(73) Assignees: Kripton Co., Ltd., Tokyo (JP); Science Technology Interact Co., Ltd., Tokyo (JP)

( * ) Notice: Subject to any disclaimer, the term of this patent is extended or adjusted under 35 U.S.C. 154(b) by 138 days.

(21) Appl. No.: 12/327,530

(22) Filed: Dec. 3, 2008

(65) Prior Publication Data

US 2009/0159457 A1    Jun. 25, 2009

Related U.S. Application Data

(62) Division of application No. 10/557,849, filed as application No. PCT/JP2004/007281 on May 21, 2004, now abandoned.

(30) Foreign Application Priority Data

May 21, 2003   (JP) ................................ 2003-143651

(51) Int. Cl.
  *B08B 3/12* (2006.01)
(52) U.S. Cl. ......... 134/1; 134/2; 134/3; 134/26; 134/27; 134/28; 134/29; 422/20; 422/28
(58) Field of Classification Search ................. 134/1, 2, 134/3, 26, 27, 28, 29; 422/20, 28, 29
See application file for complete search history.

(56) References Cited

U.S. PATENT DOCUMENTS

| 5,932,171 A | * | 8/1999 | Malchesky ...................... 422/29 |
| 6,106,691 A | | 8/2000 | Nakamura et al. |
| 2002/0017316 A1 | | 2/2002 | Ochiai |

FOREIGN PATENT DOCUMENTS

| JP | 7-275811 | | 10/1995 |
| JP | 9-28669 | | 2/1997 |
| JP | 10071391 A | | 3/1998 |
| JP | 11-070069 | * | 3/1999 |
| JP | 11-70069 | | 3/1999 |

(Continued)

OTHER PUBLICATIONS

English machine translation of JP 11-070069.

(Continued)

*Primary Examiner* — Michael Barr
*Assistant Examiner* — Saeed T Chaudhry
(74) *Attorney, Agent, or Firm* — Oblon, Spivak, McClelland, Maier & Neustadt, L.L.P.

(57) ABSTRACT

A cleaning and sterilizing method for removing organic matter adhered to the surface of an endoscopic camera instrument, and effectively exhibiting bacteria-killing and virus-killing effects of acidic water uses, as a cleaning bath, an alkaline-water-producing electrolysis bath partitioned by a separating membrane and having electrodes on both sides, and conducts preliminary cleaning of an endoscopic camera instrument inserted in the cleaning bath by ultrasonic cleaning with city tap water. Subsequently, saline solution is provided to the electrolysis bath to conduct electrolysis, conduct ultrasonic cleaning with alkaline water obtained by the electrolysis, introduce acidic water in the acidic water generation bath and conduct sterilization-cleaning, and further to conduct ultrasonic cleaning with city tap water. Then, the endoscopic camera instrument is dried with warm air as the case requires.

7 Claims, 8 Drawing Sheets

FOREIGN PATENT DOCUMENTS

| | | | |
|---|---|---|---|
| JP | 2002-045334 | * | 2/2000 |
| JP | 2001-246381 | | 9/2001 |
| JP | 2002-45334 | | 2/2002 |
| JP | 2002-263066 | | 9/2002 |
| WO | 98/29028 | | 7/1998 |

OTHER PUBLICATIONS

English machine translation of JP 2002-045334.

English machine translation of JP 10-071391.

* cited by examiner

24: CONTROL CIRCUIT
25: POWER SUPPLY

24: CONTROL CIRCUIT
25: POWER SUPPLY

METHOD FOR CLEANING AND STERILIZING ENDOSCOPIC CAMERA

TECHNICAL FIELD

The present invention relates to a method and an apparatus for cleaning and sterilizing an endoscopic camera, etc., such as an endoscope, a camera attached to this endoscope or other peripheral devices used for observing and taking a picture of an affected part of patient or for extraction of cells.

BACKGROUND ART

In general, an endoscope is to be used for inspection or medical treatment by being inserted into the body of a patient, and thus the inner walls of conduits or external surfaces of the endoscope and peripheral devices attached to the endoscope are polluted, and these devices are to be cleaned and sterilized in an endoscope cleaning apparatus after use. As such a cleaning and sterilizing method, sterilization with e.g. glutaraldehyde or peracetic acid which are harmful for human body, has been commonly used.

Recently, acidic electrolytic water obtained by electrolyzing saline solution has been gaining attention, which has a property that it has a high sterilizing power though it hardly adversely affects a human body, and a method of sterilization with such electrolytic acidic water after cleaning with water, is being introduced for use. Further, in order to compensate for a disadvantage of acidic electrolytic water that the sterilizing power is decreased when dirt or organic matter remains after the cleaning before sterilization, a method of cleaning with electrolytic alkaline water before sterilization with acidic electrolytic water, has been proposed.

Endoscopes include soft endoscopes and hard endoscopes depending on the purpose of use. However, the requirement that such needs to be cleaned and sterilized with electrolytic solution of saline solution, is common for both types of endoscopes. Further, in order to further improve the cleaning effect, a method of cleaning with e.g. city tap water before cleaning with alkaline water, or a method of cleaning with a supersonic vibration propagated in a cleaning liquid by attaching a supersonic generator to a cleaning bath, has been proposed.

Heretofore, such a method of cleaning and sterilization with electrolytic solution of saline solution, has been described, for example, in JP-A-2002-45334 (page 2 column 2 to page 3 column 3 and FIG. 1). According to this method, alkaline water and acidic water obtained by electrolyzing saline solution, are once stored in a storage bath for alkaline water and a storage bath for acidic water respectively, and these alkaline water and acidic water are supplied sequentially to a cleaning apparatus to be used for cleaning. Namely, at first, dirt as a protein adhered to the inside and outside of an endoscope is dissolved or exfoliated with the alkaline water, and then, the endoscope whose dirt is removed from to the surface, is cleaned with acidic water for sterilization. Then, in order to make the sterilization with acidic water more effective, cleaning with city tap water is conducted after the cleaning with alkaline water to wash off free dirt or alkaline water, and in order to prevent oxidation-induced deterioration or corrosion of an object to be cleaned, the object is cleaned with city tap water after the sterilization with acidic water, to remove the acidic water.

Further, as an example of ultrasonic cleaning of an endoscope, JP-A-2000-300515 (page 7 column 12 to page 8 column 13, FIG. 11 and FIG. 12) may be mentioned. The method mentioned is that an ultrasonic vibrator is attached to a tray for cleaning an endoscope, and the ultrasonic vibrator is actuated when cleaning water is supplied in the tray to conduct ultrasonic cleaning of an endoscope.

In cases of conventional cleaning and sterilizing apparatuses, as described above, an electrolysis apparatus for electrolyzing saline solution to obtain alkaline water and acidic water required for cleaning and sterilizing an endoscope, is provided separately from a cleaning and sterilizing apparatus for an endoscope. Accordingly, the alkaline water and the acidic water obtained by electrolysis of saline solution are once stored in the respective storage baths, and they are sequentially supplied to the cleaning and sterilizing apparatus. Therefore, the following problems have been caused due to the fact that the electrolysis apparatus and the cleaning and sterilizing apparatus are separately provided.

Namely, a conventional electrolysis apparatus has to be provided with not only an electrolysis bath but also storage baths respectively storing alkaline water and acidic water obtained by electrolysis. Further, in order to connect these storage baths and a cleaning bath to be used, water-feeding pipes for connecting these baths are necessary. Accordingly, entire cleaning and sterilizing apparatus including the electrolysis apparatus becomes large sized or complicated to cause an increase of production cost, and such an apparatus requires a large space for installation.

Further, due to such a large size, most of conventional cleaning and sterilizing apparatuses are required to be installed at a predetermined place for use, and a limitation exists that it is necessary to bring an endoscope to the place where the cleaning and sterilizing apparatus is installed, in order to clean and sterilize the endoscope. Therefore, such an apparatus does not have such a convenience that it is movable to the site where an endoscope is used or in the vicinity of the site, so that an endoscope can be cleaned and sterilized immediately after use, to be ready for reuse.

Further, even among conventional methods, there has been a method of cleaning an endoscope with alkaline water obtained by electrolyzing saline solution, and sterilizing the endoscope with acidic water. However, there has been a problem that cleaning with alkaline water only by immersion or a swinging movement can not achieve sufficient cleaning and takes a long time, and accordingly, satisfactory sterilizing effect can not be obtained in a subsequent cleaning step with acidic water. Namely, the sterilizing effect with acidic water is obtainable by strong oxidation power of OH radicals and chlorine radicals produced by a reaction among hypochlorous acid, chlorine gas, hydrogen peroxide and high-concentration oxygen which are dissolved in the acidic water. However, if a large amount of organic matter is present with a product to be subjected to a sterilization treatment, these radicals produced tend to be consumed to oxidize the organic matter, and radicals to be used for oxidation and sterilization of bacteria, virus or the like are reduced, whereby acidic water of unnecessarily high density is required.

Further, if, e.g., protein is present, some types of such protein become solidified under certain oxidation conditions, and the oxidation effect may become less effective to, e.g., bacteria contained in such a solidified cluster. Further, a chemical solution having unnecessarily high concentration of chlorine not only accelerates corrosion of e.g. a device to be cleaned and sterilized or a cleaning and sterilizing apparatus, but also deteriorates safety of utilization environment, and its waste water may cause environmental pollution.

The present invention has been made considering the above-mentioned problems, and it is an object of the present invention to remove the storage bath for alkaline water obtained by electrolyzing saline solution, so that e.g. an endoscope can be directly cleaned and sterilized in an electrolysis apparatus with alkaline water produced in the apparatus, to down-size a cleaning and sterilizing apparatus, and thereby to provide a method and an apparatus for cleaning and sterilizing an endoscopic camera instrument etc., which is easily moved or carried.

DISCLOSURE OF THE INVENTION

The present invention has been made to achieve the object by solving the above-mentioned problems, and the present invention provides a method and an apparatus for cleaning and sterilizing an endoscopic camera instrument etc., capable of cleaning and sterilizing an endoscopic camera instrument etc. in an alkaline-water-producing bath or in a cleaning bath connected to the alkaline-water-producing bath via a water-feeding pipe, sequentially with alkaline water and acidic water. The present invention has the following features.

The present invention is characterized by comprising conducting ultrasonic cleaning of an endoscopic camera instrument etc. with alkaline water produced by electrolysis of saline solution supplied to an electrolysis bath, to remove e.g. lipid and solid protein adhering to the endoscopic camera instrument etc., the ultrasonic cleaning with alkaline water being conducted in an alkaline-water-producing bath of the electrolysis bath or in a cleaning bath connected to the alkaline-water-producing bath via a water-supply; subsequently transferring acidic water produced by the electrolysis into the alkaline-water-producing bath or the cleaning bath; and cleaning and sterilizing the endoscopic camera instrument etc. with the acidic water.

Further the present invention is characterized by preferably conducting preliminary cleaning of an endoscopic camera instrument etc. with water; conducting ultrasonic cleaning of the endoscopic camera instrument etc. with alkaline water produced by electrolysis of saline solution supplied to an electrolysis bath, to remove e.g. lipid and solid protein adhering to the endoscopic camera instrument etc., the ultrasonic cleaning with alkaline water being conducted in an alkaline-water-producing bath of the electrolysis bath or in a cleaning bath connected to the alkaline-water-producing bath via a water-supply; subsequently cleaning and sterilizing the endoscopic camera instrument etc. with acidic water produced by the electrolysis; and conducting cleaning of the endoscopic camera instrument etc. with water; followed by drying the endoscopic camera instrument etc. with warm air as the case requires.

A preferred embodiment of the present invention is characterized in that the method uses as the cleaning bath the alkaline-water-producing bath of the electrolysis bath, the electrolysis bath having electrodes on both sides and partitioned by a membrane; the method comprising conducting preliminary cleaning of the endoscopic camera instrument etc. inserted into the cleaning bath by ultrasonic cleaning with water; conducting ultrasonic cleaning of the endoscopic camera instrument etc. with alkaline water produced by electrolysis of saline solution supplied to the electrolysis bath; subsequently draining the alkaline water from the alkaline-water-producing bath and supplying acidic water stored in an acidic-water-producing bath into the alkaline-water-producing bath; sterilizing and cleaning the endoscopic camera instrument etc. with the acidic water; and further conducting cleaning of the endoscopic camera instrument etc. with water; followed by drying the endoscopic camera instrument etc. with warm air as the case requires.

Further, another preferred embodiment of the present invention is characterized in that an acidic-water-producing bath of a water-flow type electrolysis bath is connected to the cleaning bath via a second water-feeding pipe; acidic water produced in the alkaline-water producing bath, is supplied to the cleaning bath to conduct cleaning of the endoscopic camera instrument etc., and the acidic water is supplied to the cleaning bath through the alkaline-water-producing bath to conduct sterilization.

Further the present invention is characterized by comprising an alkaline-water-producing-cleaning bath, and an acidic-water-producing bath, which are formed by partitioning an electrolysis bath having electrodes on both sides by a membrane; the electrolysis bath being provided with a first water-feeding pipe for supplying water and a second water-feeding pipe for supplying saline solution; the alkaline-water-producing-cleaning bath being provided with draining means and an ultrasonic generator; and the alkaline-water-producing-cleaning bath and the acidic-water-producing bath communicating with each other via a control valve and a pump; wherein the apparatus is configured to conduct ultrasonic cleaning of the endoscopic camera instrument etc. with alkaline water obtained by electrolyzing saline solution supplied to the electrolysis bath, and subsequently to conduct sterilization of the endoscopic camera installment etc. with acidic water transferred from the acidic-water-producing bath into the alkaline-water-producing-cleaning bath; followed by conducting cleaning with water.

Further, the present invention is characterized by comprising a cleaning bath provided with an ultrasonic generator and draining means, a water-flow type electrolysis bath having an alkaline-water-producing bath and an acidic-water-producing bath formed on both sides of a membrane; the cleaning bath and the water-flow type electrolysis bath being connected via a water-feeding pipe; the alkaline-water-producing bath and the acidic-water-producing bath having inlets for receiving saline solution and outlets for draining alkaline water and acidic water obtained by electrolyzing saline solution; and the outlet of the acidic-water-producing bath communicating with the cleaning bath through the alkaline-water-producing bath with or without intervention of a storage tank; wherein the apparatus is configured to conduct ultrasonic cleaning of an endoscopic camera instrument etc. inserted in the cleaning bath, with alkaline water supplied from the alkaline-water-producing bath, sterilize the endoscopic camera instrument etc. with acidic water transferred into the cleaning bath through the alkaline-water-producing bath, and subsequently clean the endoscopic camera instrument etc. with water transferred to the cleaning bath.

BEST MODE FOR CARRYING OUT THE INVENTION

Objects to be cleaned and sterilized by the present invention includes endoscopic camera instruments including endoscopes, cameras attached to the endoscopes and other peripheral devices, and operation tools such as forceps, and implants. An endoscopic camera instrument etc. in the present invention is a generic name of these. Further, an endoscope includes both of hard type and soft type.

Therefore, an endoscopic camera instrument means each of an endoscope and its peripheral devices, or a combination of them. Further in a case of a soft type endoscope requiring cleaning of inside of its conduit, the endoscope and peripheral devices to be attached to this are cleaned in a state that they are separated. On the other hand, in a case of a hard type endoscope not requiring cleaning of inside of its conduit, it can be cleaned in a state that a camera and peripheral devices such as camera cables and optical cable connectors are connected to a main unit attached with an inserting portion. Thus, a hard type endoscope is more suitable for the cleaning of the present invention in that complete set of used endoscope can be cleaned and sterilized as it is.

In the present invention, in a case where an endoscopic camera instrument etc. is inserted into a cleaning bath to be cleaned, the endoscopic camera instrument etc. may be accommodated as it is stood in a vertical cleaning bath having a certain depth, or the endoscopic camera instrument etc. may be accommodated as it is laid down horizontally in a cleaning bath having a shape (a vat shape) having a wide opening and shallow depth. Further, in a case of e.g. a hard type endoscope where the endoscope is accommodated in a cleaning bath in a state that the endoscope is connected with a camera, a large cleaning bath is usually required.

Further, in the present invention, usually common salt (sodium chloride) is used for the saline solution for electrolysis. However, an aqueous solution of a material other than common salt, such as aqueous solution of potassium chloride, may be used. Further, as the water for the cleaning of the present invention, normal city tap water is used as it is for the reason of cost and convenience unless there is particular problem with city tap water. However, depending on the type of object to be cleaned or the degree to be cleaned, softened water from which e.g. potassium and magnesium contained in city tap water are removed, an ion-exchanged water from which cation and anion are removed, RO water which is filtered by a half-semipermeable membrane, or a purified water may also be used.

Figure 1:
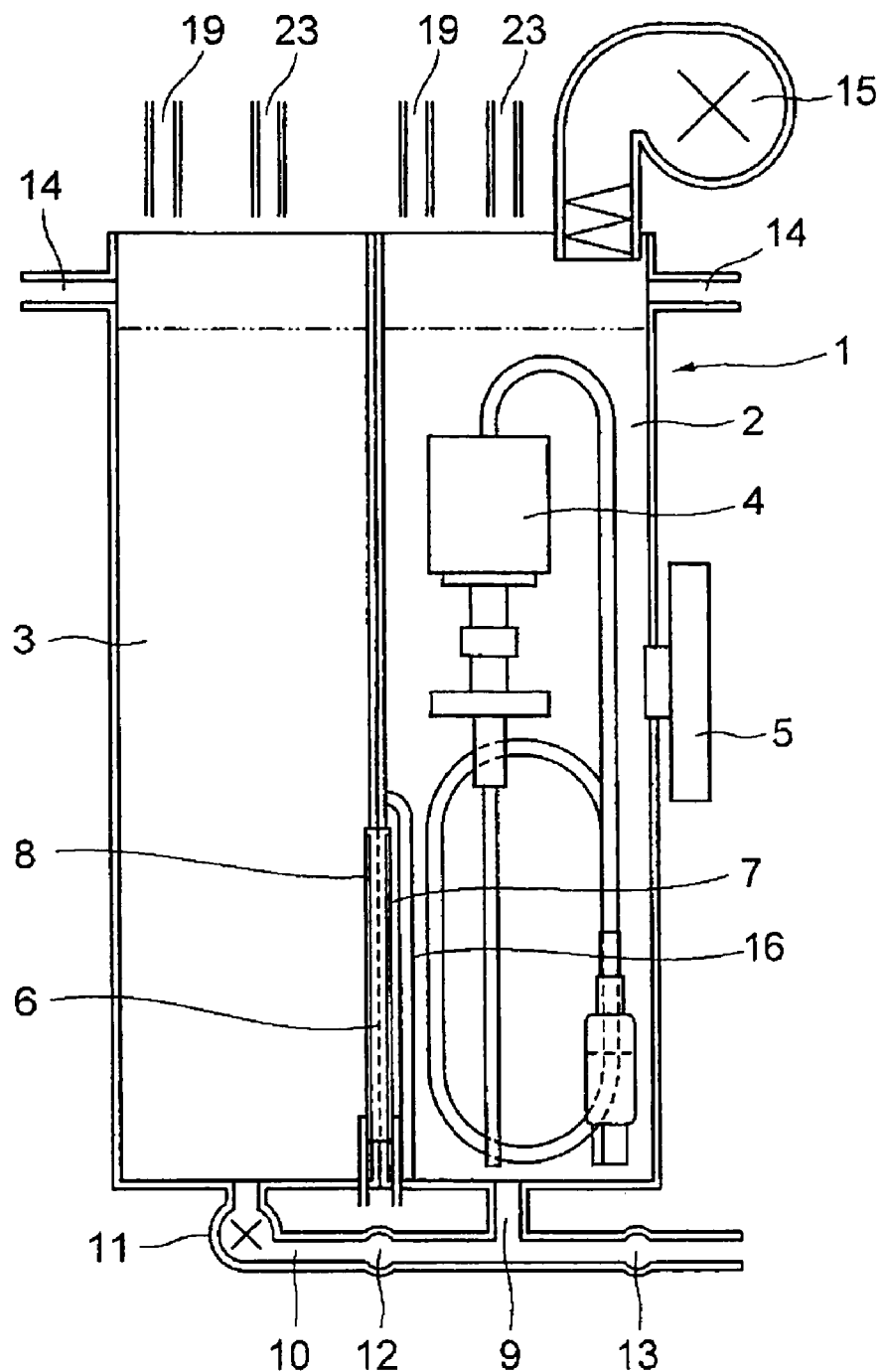
FIG. 1 is a cross-sectional view of a preferred embodiment of the cleaning and sterilizing apparatus of the present invention.
Figure 2:
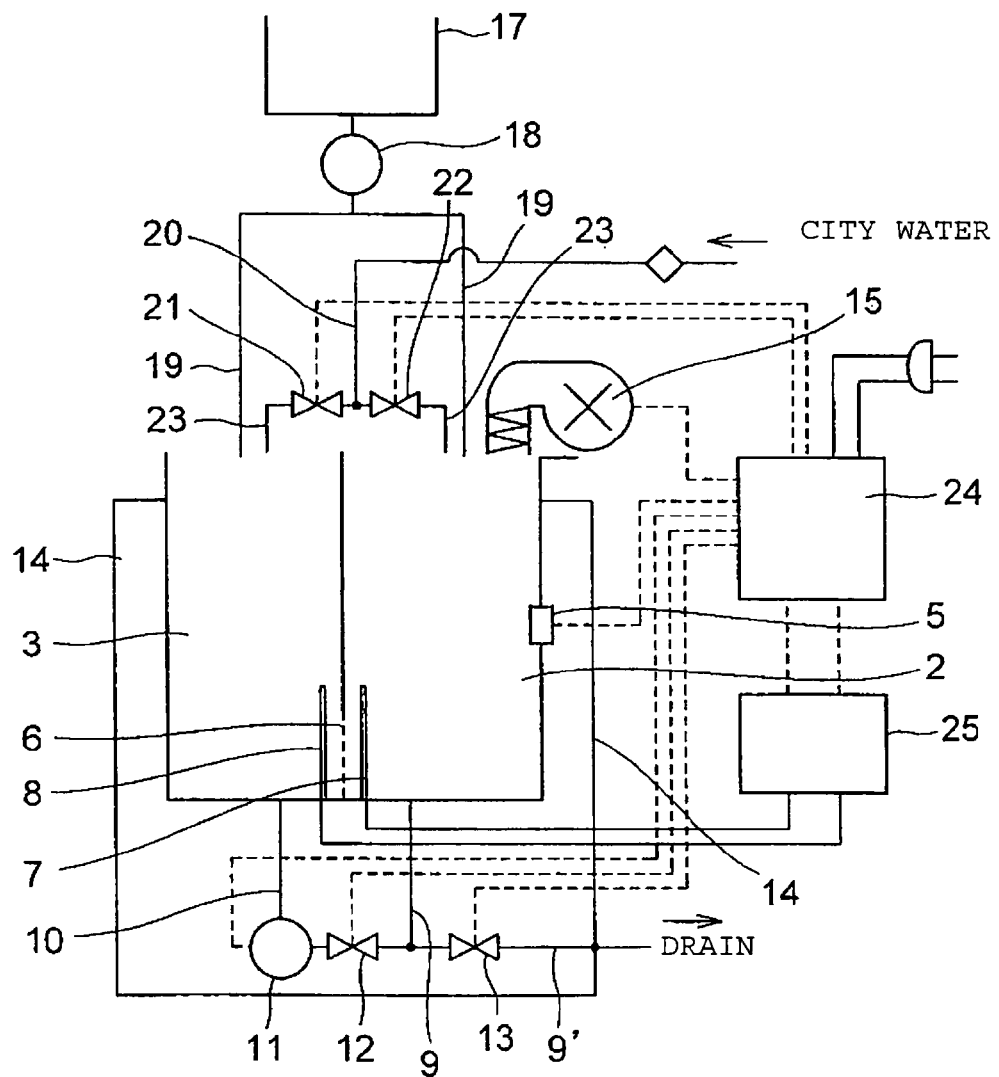
FIG. 2 is a system diagram of the entire control system of the cleaning and sterilizing apparatus of FIG. 1.

Next, a preferred embodiment of the present invention will be described with reference to FIG. 1 and FIG. 2. This example is of a cleaning and sterilizing apparatus using an alkaline-water-producing bath of an electrolysis bath as a cleaning bath, which uses aqueous solution of common salt as the saline solution for electrolysis. FIG. 1 is a cross-sectional view of this cleaning and sterilizing apparatus, and FIG. 2 is a system diagram showing the construction of entire system of the apparatus. As shown in FIG. 1, an electrolysis bath 1 is partitioned by a separating membrane 6, into an alkaline-water-producing bath 2 as a cathode chamber and an acidic-water-producing bath 3 as an anode chamber. A cathode 7 and an anode 8 are provided on both sides of the separating membrane 6, and the cathode 7 and the anode 8 electrolyzes saline solution poured into the electrolysis bath 1 in the same manner as a normal electrolysis bath, to produce alkaline water and acidic water. Such a separating membrane is required to have as small water permeability as possible, and an ion-exchange membrane is preferably used as such a separating membrane.

The alkaline-water-producing bath 2 not only functions as a cathode chamber of the electrolysis bath but also serves as a cleaning bath at the same time. Namely, the alkaline-water-producing bath 2 is an alkaline-water-producing-cleaning bath (hereinafter it is simply referred to as a cleaning bath). Accordingly, the cleaning bath has a deep vertical shape as a suitable structure for an electrolysis bath, and has a volume of about from 7 to 10 L, whereby an endoscopic camera instrument 4 can be inserted vertically as it is assembled. In order to protect the cathode 7 from the endoscopic camera instrument 4, a guardgrill is provided in the outer side of the cathode 7. Further, a hook may be provided to the upper portion of a side wall in the cleaning bath 2 though such a hook is not shown in FIG. 1, so that an endoscopic camera instrument 4 can be hung on the hook so that the endoscopic camera instrument 4 can be easily cleaned.

In the electrolysis bath 1, each of the cleaning bath 2 and the acidic-water-producing bath 3 is provided with a water-feeding pipe 19 for supplying saline solution and a water-feeding pipe 23 for supplying city tap water. The water-supply pipe 19 for supplying saline solution is communicated with a saline solution tank 17 via a pump 18 as shown in FIG. 2. When an endoscopic camera instrument 4 is cleaned with alkaline water in the cleaning bath 2, a predetermined amount of saline solution is continuously or intermittently supplied to the electrolysis bath 1 by the pump 18.

Meanwhile, the water-feeding pipe 23 for supplying city tap water is communicated with city tap water lines via control valves 21 and 22 and a water-feeding pipe 20. When an endoscopic camera instrument 4 is preliminarily cleaned in the cleaning bath 2, when it is necessary to dilute saline solution supplied through the water-feeding pipe 19 to adjust the concentration, when rinsing is necessary after an alkaline water cleaning, or when cleaning with city tap water is conducted after sterilization with acidic water, city tap water is supplied to the cleaning bath 2 by open/close operation of the control valve 22 as the case requires. Since appropriately cleaned and sterilized city tap water, has an advantage that it is easily obtainable, the city tap water is usually used as a water source in this Example. However, water other than city tap water may also be used so long as it is clean water. Further, the last cleaning to be conducted after sterilizing treatment with acidic water, is preferably carried out with an aseptic water obtained by further sterilizing city tap water.

Underneath the cleaning bath 2 of the electrolysis bath 1, a drain pipe 9, a control valve 13 and a drain pipe 9' are provided as draining means. Further, by connecting a pipe 10 having one end opening in a lower part of the acidic-water-producing bath 3 with the drain pipe 9 at a portion between the cleaning bath 2 and the control valve 13, the cleaning bath 2 and the acidic-water-producing bath 3 are communicated. In the pipe 10, a water-supply pump 11 and a control valve 12 are provided so that acidic water in the acidic-water-producing bath 3 can be supplied to the cleaning bath 2 by the water-supply pump 11 when the control valve 12 is opened in a state that the control valve 13 in the drain pipe 9 is closed. Further, by thus connecting the pipe 10 with the drain pipe 9 and opening the control valves 12 and 13, unnecessary acidic water in the acidic-water-producing bath can be appropriately wasted through the drain pipe 9'.

Further, in the upper portions of the side walls of the cleaning bath 2 and the acidic-water-producing bath 3, respective drain pipes 14 are provided to maintain the water levels of these baths to predetermined levels. These drain pipes 14 are connected with the drain pipe 9' as shown in FIG. 2, so that overflowed water is automatically drained to the drain pipe 9' when the water levels of these baths exceed predetermined levels.

Further, the cleaning bath 2 is provided with an ultrasonic generator 5 and a warm-air apparatus 15. The ultrasonic generator 5 is to impart an ultrasonic cleaning function to the cleaning bath 2 to conduct an ultrasonic cleaning of an endoscopic camera instrument 4, as described later. Specifically, the ultrasonic generator 5 generates ultrasonic waves at a time of cleaning with alkaline water, and it generates ultrasonic waves also at times of preliminary cleaning with city tap water and finishing cleaning to be conducted after sterilization treatment with acidic water as the case requires. The cleaning bath 2 is made of a resin or a metal having high corrosion resistance so that the cleaning bath 2 has corrosion resistance against acid and alkali. In the case of resin, in order to effectively propagate ultrasonic waves to cleaning water, it is preferred to use a stainless steel coated with a resin for a part of the cleaning bath 2 connected with an ultrasonic-generating element. Further, if the cleaning bath 2 is made of YUS-270 manufactured by Nippon Steel and Sumikin Stainless Steel Corp. or SUS317L, ultrasonic generation efficiency and OH radical generation efficiency can be improved though the cost is slightly increased.

In the cleaning and sterilizing apparatus, these constituents are automatically controlled as described later. By setting cleaning conditions in advance, it is possible to automatically conduct operations from preliminary cleaning to sterilization with acidic water or to cleaning after the sterilization. Further, warm-air drying can also be automatically controlled. Specifically, a plurality of programs are prepared in advance based on the degree of dirtiness and the size of an endoscopic cameral instruments to be cleaned and sterilized (object to be cleaned). By selecting a desired program from these programs depending on the object to be cleaned, automatic cleaning can be carried out in accordance with the program.

Next, a method of cleaning and sterilizing an endoscopic camera instrument by employing the apparatus will be described with reference to FIG. 2. The endoscopic camera instrument 4 of this example is a hard-type endoscope, and it is inserted in its entirety into the cleaning bath 2 in vertical direction to be accommodated in a state that a camera is connected with the main body of the endoscope (refer to FIG. 1). Then, the water-feeding pipe 20 is connected with a city tap water line. Then, a control valve 22 is opened in a state that a control valve 21 and a control valve 13 are closed as instructed by a control circuit 24, so that city tap water is supplied to the cleaning bath 2 through a water-feeding pipe 23. When the city tap water level in the cleaning bath 2 approximately reaches a predetermined level, an ultrasonic generator 5 is started to conduct preliminary cleaning. During the preliminary cleaning, the city tap water is usually continuously supplied to the cleaning bath 2. However, ultrasonic cleaning may also be conducted in a state that supply of city tap water is stopped at a predetermined level of city tap water. The ultrasonic cleaning with city tap water is conducted, for example, for 3 minutes to sufficiently remove water-soluble dirt of the endoscopic camera instrument 4.

When the preliminary cleaning is completed, the control valve 22 is closed and the control valve 13 is opened at the same time to drain the city tap water in the cleaning bath. Then, a pump 18 is started to supply saline solution from a saline solution tank 17 to the electrolysis bath 1 (the cleaning bath 2 and the acidic-water-producing bath 3) through a water-supply pipe 19. At this time, if the salt concentration is too high, the saline solution is diluted with city tap water by appropriately opening control valves 21 and 22.

Then, electricity is supplied from an electrolysis power supply 25 to the anode 8 and the cathode 7 of the electrolysis bath 1 to electrolyze the saline solution. By this electrolysis, alkaline water is produced in the cleaning bath 2 and acidic water is produced in the acidic-water-producing bath 3. In this state, ultrasonic vibration is applied from an ultrasonic generator 5 to the alkaline water in the cleaning bath to conduct alkaline-water-ultrasonic cleaning, for example, for 5 minutes. During the ultrasonic cleaning, the saline solution is supplied continuously or intermittently at a predetermined interval to the electrolysis bath 1 so as to adjust the supply amount of saline solution to the electrolysis capacity, whereby an endoscopic camera instrument can be cleaned while the electrolysis is being conducted. However, it may be such that the supply of saline solution is stopped when the cleaning bath 2 is filled with the saline solution, and the electrolysis of saline solution supplied to the electrolysis bath 1 and ultrasonic cleaning with the alkaline water generated by the electrolysis, are conducted in this state. The alkaline water used for cleaning is drained to the outside through a drain pipe 14.

When an endoscopic camera instrument 4 is cleaned in the alkaline-water-producing bath 2 of the electrolysis bath 1 as in this example, stronger cleaning effect can be obtained as compared with the cleaning using alkaline water obtained by electrolysis and once reserved in a reservation tank. The reason for this is assumed to be that the alkaline water of the present invention containing hydrogen gas produced at a time of electrolysis, provides stronger cleaning effect than that of a sodium hydroxide aqueous solution having the same pH. Further, by applying ultrasonic waves, the cleaning power can further be increased.

By the ultrasonic cleaning with alkaline water, dirt adhered to an endoscopic camera instrument such as lipid or solidified protein, particularly, blood or organic matter derived from lipid of human body, can be satisfactorily removed. By thus removing organic matter preventing the oxidation-sterilization power of acidic water, from the surface of the endoscopic camera instrument, bacteria-killing and virus-killing effects of acidic water can be more effectively exhibited in the subsequent step. Particularly, if ultrasonic cleaning with city tap water is conducted in the preliminary cleaning step, the effect of alkaline-water-cleaning can further be increased.

When the alkaline-water-cleaning is completed, the supply of saline solution is stopped, the powers of electrolysis power supply 25 and the ultrasonic generator 5 are turned off, and the control valve 13 is opened to drain the alkaline water 2 in the cleaning bath 2 though the drain pipe 9. Then, it is preferred that city tap water is supplied to the cleaning bath from which alkaline water is drained, to rinse the cleaning bath 2 in the same manner as the above-mentioned preliminary cleaning. The time for rinsing is preferably about 2 to 3 minutes. After the rinsing, water in the cleaning bath is drained. Then, the control valve 13 is closed and the control valve 12 is opened to supply the acidic water reserved in the acidic-water-producing bath 3 to the cleaning bath 2 for sterilization. The sterilization can be easily carried out by immersing the endoscopic camera instrument in the acidic water poured in the cleaning bath 2 for a predetermined time. In this example, this immersion time is about 10 minutes.

In the present invention, since the acidic water is thus moved to the cleaning bath 2 (alkaline-water-producing bath) to conduct sterilization, even if calcium or magnesium in city tap water precipitates on an electrode or a portion of the alkaline-water-producing bath in contact with water level, a layer of such precipitated product can be dissolved and removed by the acidic water.

When the sterilizing treatment with acidic water is completed, the control valve 13 is opened to drain the acidic water in the cleaning bath 2, and then, city tap water is supplied to the cleaning bath 2 is to clean the bath for 3 minutes. At this time, the cleaning can be conducted efficiency in a short time by applying ultrasonic waves. By this cleaning with city tap water, since acidic water remaining on the surface or between gaps of the endoscopic camera instrument can be removed, an anti-corrosion effect can be obtained. Further, since the dead bodies of bacteria, oxide product or decomposed product of dirt produced as a result of the sterilization-cleaning with acidic water, can be removed by the water-cleaning, a nutrition source as a source for re-pollution can be sufficiently removed and the endoscopic camera instrument can be maintained with cleanness.

Then, after city tap water in the cleaning bath 2 is drained, a warm-air apparatus 15 is started to supply warm air in the cleaning bath to dry the cleaned and sterilized endoscopic camera instrument. The endoscopic camera instrument etc. sterilized and cleaned with acidic water and cleaned with water, is usually dried with warm air as in this example. However, in the present invention, this drying may be carried out as the case requires, and the drying is also possible by supplying air only.

Thus, since a single bath serves both as cleaning bath and alkaline-water-producing bath in this example, space-saving can be achieved as compared with the case of providing an electrolysis bath and a cleaning-sterilizing bath independently. Further, since after the cleaning with alkaline water, acidic water is moved to the alkaline-water-producing bath for sterilization, calcium or magnesium present in city tap water and precipitated on an electrode or a portion of the alkaline-water-producing bath in contact with water level at a time of producing alkaline water, is dissolved and removed by the acidic water, and conventional maintenance such as exchange of polarities of electrodes for electrolysis or cleaning with acid water, becomes unnecessary.

Here, in the preliminary cleaning before the alkaline-water-cleaning or in the rinsing after the sterilization-cleaning with acidic water, a high cleaning effect can be obtained by applying ultrasonic wavers as in this example. However, these cleaning steps may be a stirring-cleaning with cleaning liquid or simple city-water-cleaning if decrease of cleaning effect is acceptable.

In the above, an example of the cleaning and sterilizing apparatus of the present invention has been described. However, the cleaning and sterilizing apparatus may further be modified or improved. For example, although waster water of the cleaning bath is drained by natural draining in this example, the waste water may be drained by forced draining by providing a drain pump to the draining means. By thus utilizing the drain pump or by expanding the drain pipe of the cleaning bath or the water passage of the control valve, draining time can be reduced. Further, such a drain pump enables draining to a drain port located at a higher position than the draining portion of the apparatus. Accordingly, such a modification makes the apparatus usable in wider range of locations, and is effective also for a large-sized cleaning and sterilizing apparatus.

Further, the cleaning bath 2 may be provided with a heating device (for example, an electrical heater) or a stirring device as has been conducted in conventional apparatuses. If the cleaning bath 2 is provided with a heating device, e.g. cleaning water can be heated at, for example, about 40° C. as the case requires, whereby cleaning effect can be increased. If alkaline water, acidic water or city tap water is stirred in the cleaning bath by such a stirring device, water flow is generated to effectively remove lipid or solidified protein adhered to the surface of the object to be cleaned, and to satisfactorily clean and sterilize fine portions or gaps of the object to be cleaned. Here, most of these modifications in this example or items conducted in this example, are not limited to this example and may be applied to other examples in the same manner.

Then, another preferred embodiment of the present invention will be described with reference to FIGS. 3 to 8. In this example, a cleaning-sterilizing bath (cleaning bath) and a water-flow type electrolysis bath are communicated via a water-feeding pipe, and they are combined with a saline solution tank, an acidic water tank and the like to constitute a unit as a whole, whereby alkaline water obtained in the water-flow type electrolysis bath can be directly supplied to the cleaning bath. Since such a construction can simplify the design of the water-flow type electrolysis bath, it is possible to make entire cleaning apparatus easily portable and small-sized. Accordingly, in the same manner as the above-mentioned method of cleaning and sterilization in the bifunctional bath used as alkaline-water-producing bath and cleaning bath, it becomes possible to bring the cleaning apparatus to e.g. a site where an endoscope is used, to clean the endoscope at the site of use, enabling repeated use of the endoscope.

Figure 3:
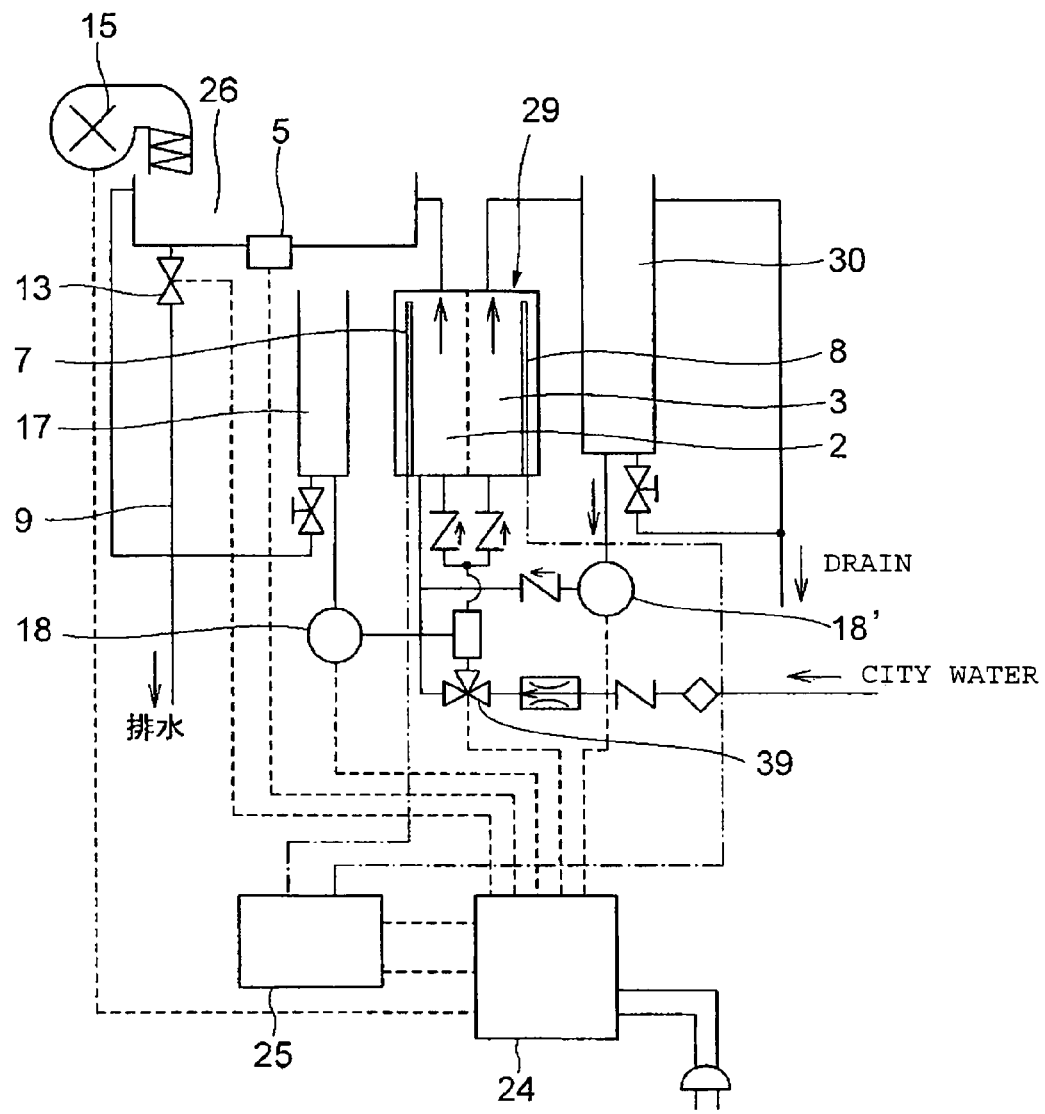
FIG. 3 is a system diagram of another embodiment of the control system of the cleaning and sterilizing apparatus of the present invention.
Figure 4:
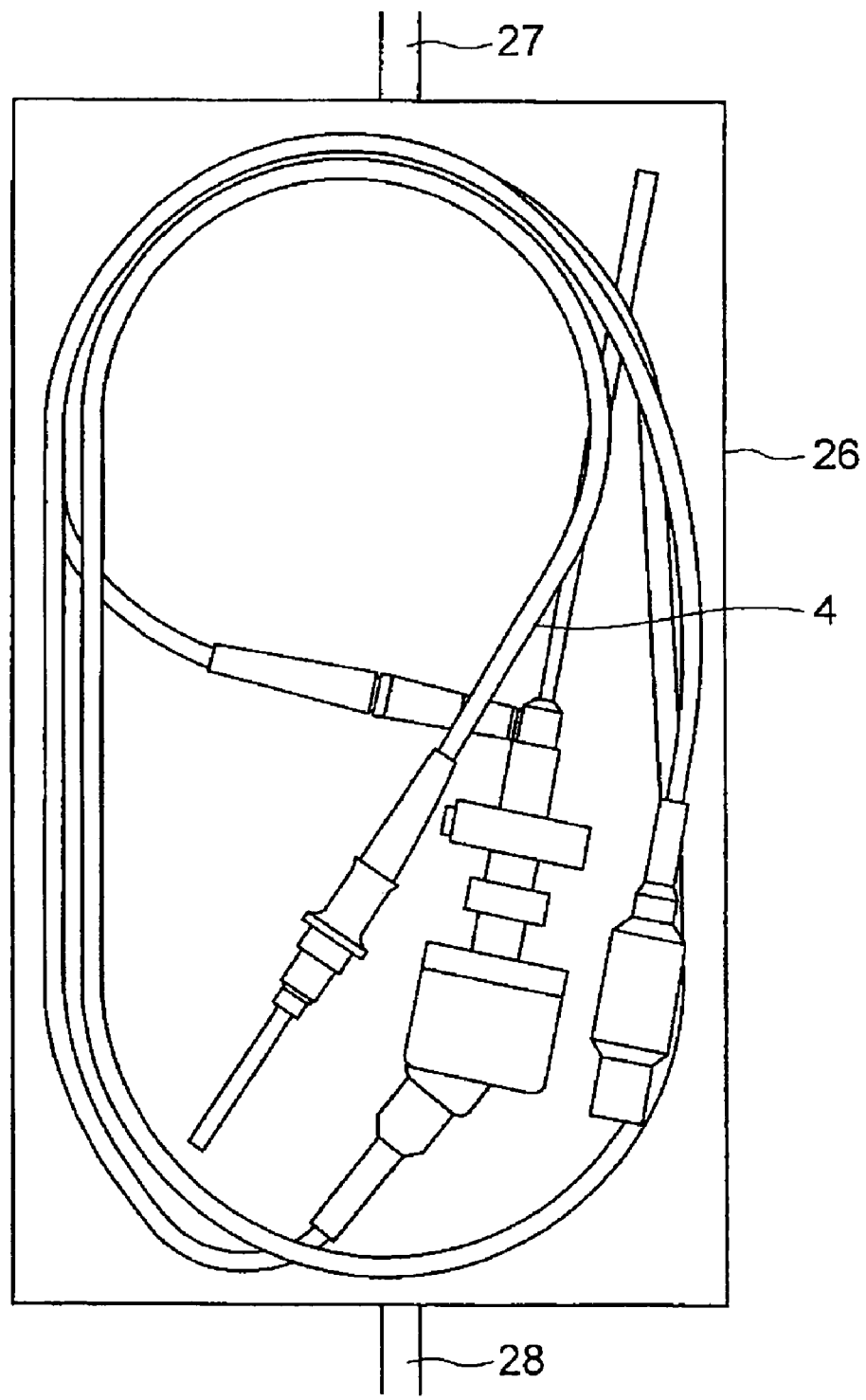
FIG. 4 is a plan view of the cleaning and sterilizing bath of the cleaning and sterilizing apparatus of FIG. 3.

FIG. 4 is a schematic plan view of the cleaning-sterilizing bath. The cleaning sterilizing-bath 26 has a rectangular cubic shape, and is made of a resin such as PP or PET having durability against cleaning liquid or sterilizing liquid, or made of e.g. a metal having high corrosion resistance such as titanium or a stainless steel having durability against acid and salt. The cleaning-sterilizing bath 26 has an inner volume large enough to accommodate an endoscope and a camera as they are connected as shown in FIG. 4, and its side wall is provided with a water supply port 27 to be connected to a water-flow type electrolysis bath to receive cleaning-sterilizing liquid or city tap water, and a drain port 28 for draining e.g. cleaning liquid after use (refer to FIG. 3).

Further, the bottom of the cleaning-sterilizing bath 26 is provided with an ultrasonic generator 5 that is not shown in FIG. 4 (refer to FIG. 3).

The cleaning-sterilizing bath 26 of this example is preferably one having a relatively shallow depth and a large opening. Such a shape enables to accommodate an endoscopic camera instrument 4 in horizontal direction as shown in FIG. 4, and facilitates placing/retrieving of the instrument in/from the cleaning sterilizing bath to improve workability. However, the shape and the size of the cleaning-sterilizing bath 26 is preferably determined depending on the object to be cleaned.

Figure 5:
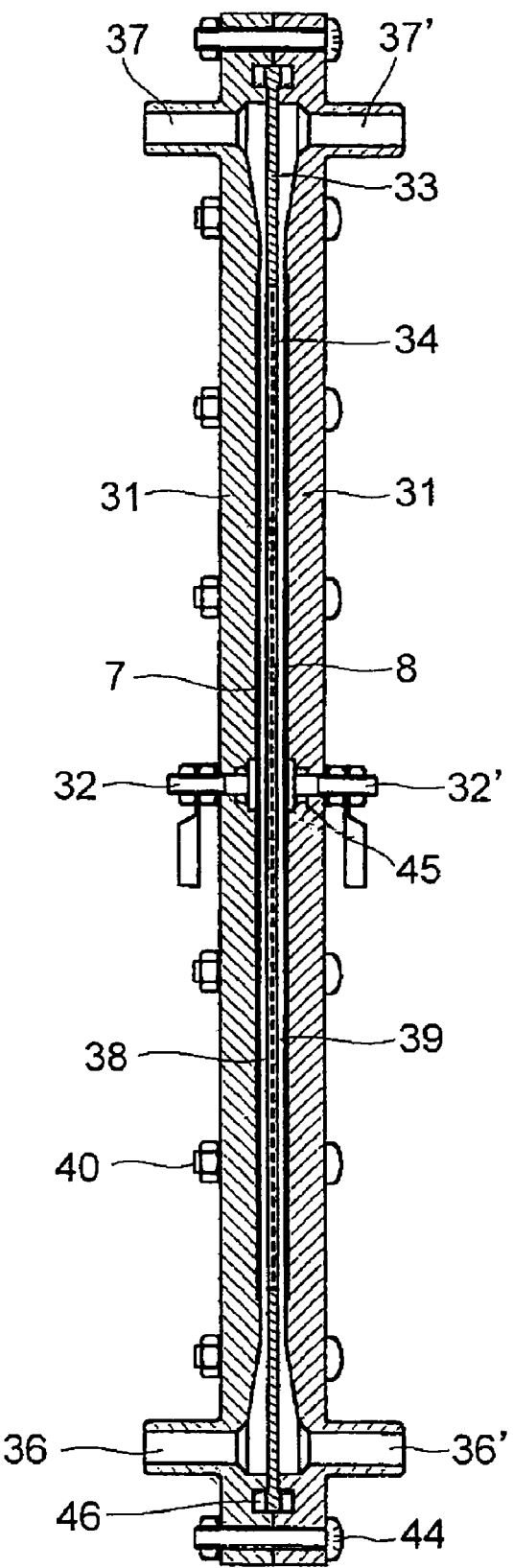
FIG. 5 is a cross-sectional view of the water-flow type electrolysis bath in the cleaning and sterilizing apparatus of FIG. 3.

Then, an example of water-supply type electrolysis bath is described with reference to drawings. FIG. 5 is a cross-sectional view of the water-flow type electrolysis bath of this example. The water-flow type electrolysis bath is constituted by a separating membrane frame 33 provided with a separating membrane 34; one pair of electrolysis bath casings 31 having respective inner faces opposing to each other, having a cathode 7 and an anode 8 respectively, and sandwiching the separating membrane frame 33; and screws 40 fastening the peripheral portions of the electrolysis bath casings 31 together. In this opposing inner faces of the electrolysis bath casings 31, the respective recesses 35 (refer to FIG. 7) are formed and inner faces of these recesses are provided with the cathode 7 and the anode 8 respectively, so that electricity is supplied from a cathode terminal 32 and an anode terminal 32' provided in the central portions of the respective electrolysis bath casings 31, to these electrode 7 and anode 8 respectively.

Then, the spacing between the above-mentioned separating membrane 34 and the cathode 7 serves as an alkaline-water-producing bath (cathode chamber) 38, and a space between the separating membrane 34 and the anode 8 serves as an acidic-water-producing bath (anode chamber) 39. To the alkaline-water-producing bath 38 and the acidic-water-producing bath 39, a saline solution is supplied from water-inlet ports 36 and 36' respectively, and the supplied saline solution is electrolyzed in the alkaline-water-producing bath 38 and the acidic-water-producing bath 39. Thus produced alkaline water and acidic water are taken out from water-outlet ports 37 and 37' respectively. In order to increase water tight of the water-flow type electrolysis bath, gaskets 46 and gaskets 45 for sealing are inserted between the separating membrane frame 33 and the electrolysis bath casings 31, and between the electrolysis bath casings 31 and the electrode terminals, respectively.

Figure 6:
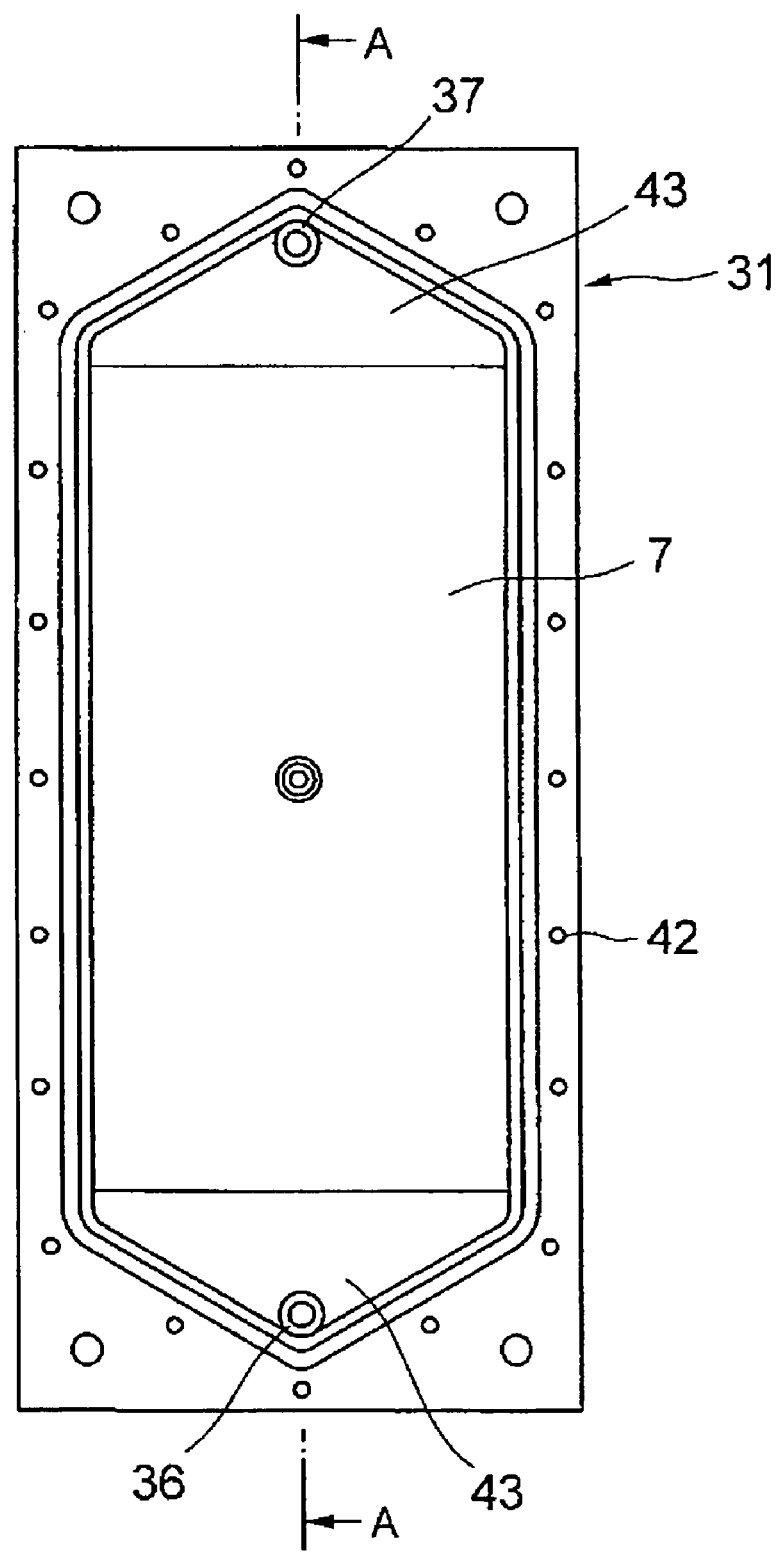
FIG. 6 is a front view of one of the electrolysis bath casing of the water-flow type electrolysis bath of FIG. 5.
Figure 7:
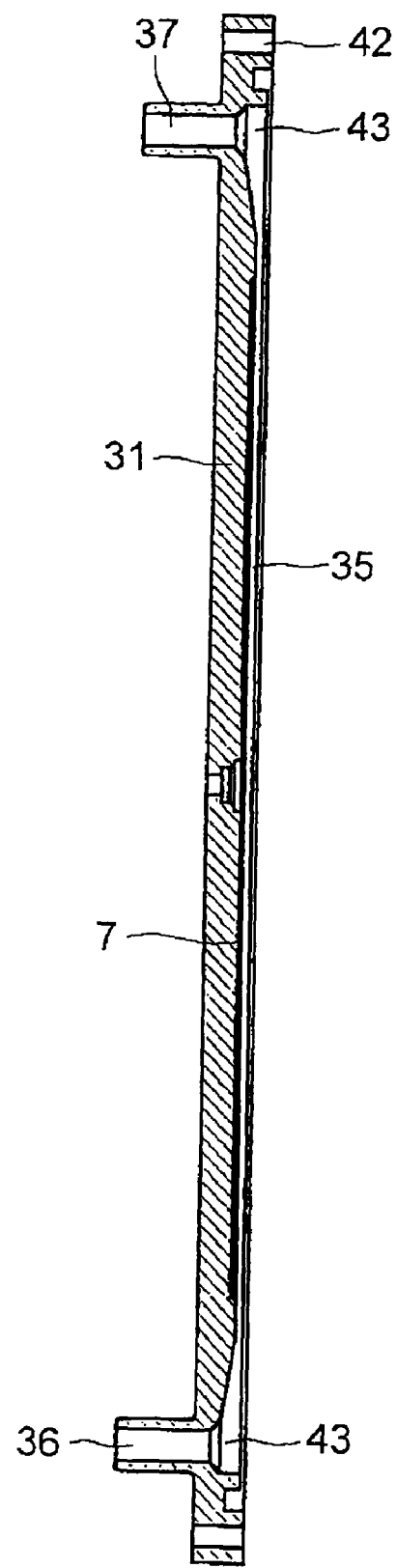
FIG. 7 is a cross-sectional view at A-A portion of FIG. 6.
Figure 8:
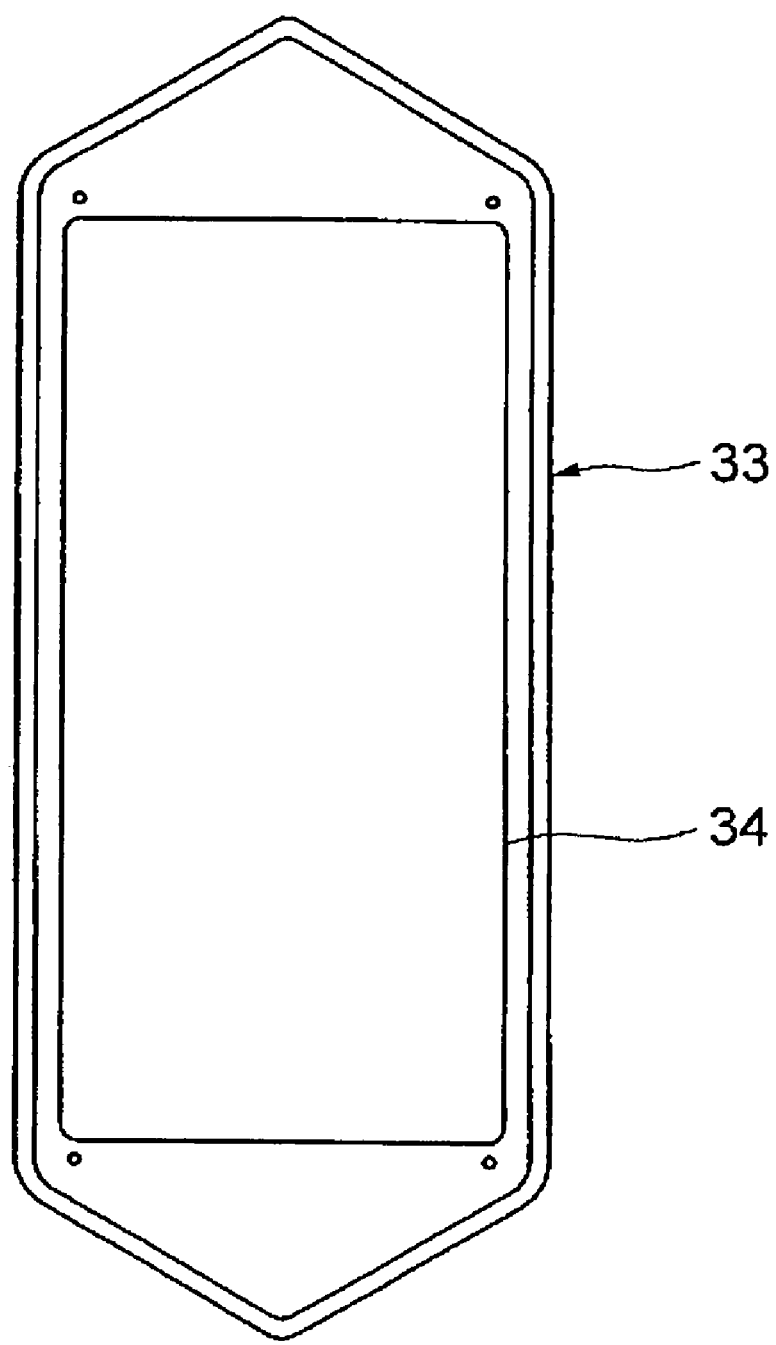
FIG. 8 is a front view of a separating-membrane frame in the water-flow type electrolysis bath of FIG. 5.

FIG. 6 is a front view of the electrolysis bath casing 31 of the cathode side, and FIG. 7 is a cross-sectional view at A-A portion of FIG. 6. FIG. 8 shows the separating membrane 34 for electrolysis, to be combined with the electrolysis bath casings 31 to constitute the water-flow type electrolysis bath. The separating membrane 34 is spread and fixed by a thin separating membrane frame 33 made of resin. Here, since the electrolysis bath casing 31 of the anode side is symmetry to the electrolysis bath casing 31 of the cathode side, only the electrolysis casing of the cathode side will be described here.

The electrolysis bath casing 31 is, as shown in FIG. 6, a rectangular plate-shaped member having one surface in which a recess 33 having a predetermined width and depth is formed in the longitudinal direction of the plate-shaped member so as to fit the shape of the separating membrane frame 33. Further, in the peripheral portion of the electrolysis casing 31, a plurality of holes 42 for screws are provided for tightly connecting the electrolysis bath casing with an electrolysis bath casing of anode side, with screws 40 (refer to FIG. 5). Upper and lower parts of the recess 35 have upward and downward chevron shapes towards the upper and the lower ends of the plate-shaped member respectively as shown in FIG. 6. The depth of the recess at each of the chevron portions 43 increases towards the tip as shown in FIG. 7, and a water-inlet port 36 and a water-outlet port 37 are provided for convenience at the respective deepest portions of the recess, namely at the summits of the respective chevron portions 43. By thus forming the chevron portions 43 of the recess, supply of saline solution to the electrolysis bath and taking out of alkaline water and acidic water produced by electrolysis can be carried out smoothly. Further, since electrolyte flows through the electrolysis bath uniformly, uniform electrolysis can be obtained over the entire separating membrane 34.

Inside the recess 35, a cathode 7 is provided in the region corresponding to the separating membrane 34. Thus the separating membrane 34 is sandwiched from both sides with the electrolysis-bath-casing 31 having a recess provided with the cathode 7 therein and the electrolysis-bath-casing of the anode side provided with the anode 8, whereby the cathode 7 is placed with a distance corresponding to the recess from the separating membrane 34 to form a spacing between them, and the spacing forms an alkaline-water-producing bath. Further, in the opposite side of the separating membrane 34, an acidic-water-producing bath is formed.

In this example, the depth of the recess 35 is preferably within a range of from 1 to 10 mm. If the recess is deeper than 10 mm, the distance between the electrode and the separating membrane becomes too large, and the electrical resistance at a time of electrolysis increases and the electrolysis efficiency decreases, such being not preferred. Further, on the contrary, if the recess is shallower than 1 mm, the electrode and the separating membrane become too close, which may cause abnormal wearing of the electrode surface due to contact between the electrode and the separating membrane, increase of water flow resistance or uneven distribution of water flow.

FIG. 3 is a system piping diagram of a system, in which the water-flow type electrolysis bath 29 of this example and a cleaning-sterilizing bath 26 are connected for automatically cleaning and sterilizing an endoscopic camera instrument. The cleaning method with this apparatus is specifically described with reference to the system piping diagram. However, the basic concept of the cleaning and sterilizing is the same as the above-mentioned method of FIG. 2. At first, a city tap water line is connected with this apparatus, and an endoscopic camera instrument to be cleaned, is accommodated in the cleaning sterilizing bath 26. Then, a control valve 39 is opened to supply city tap water to the cleaning-sterilizing bath 26 through the alkaline-water-producing bath 2 of the water-flow type electrolysis bath 29. In this case, city tap water may be directly supplied to the cleaning-sterilizing bath 26 without flowing through the alkaline-water-producing bath 2. However, by flowing city tap water through the alkaline-water-producing bath 2, the apparatus can be simplified and the alkaline-water-producing bath can be cleaned with the city tap water flown through the bath.

An ultrasonic generator 5 is actuated as city tap water is supplied to the cleaning-sterilizing bath 26, to preliminarily clean an endoscopic camera instrument by ultrasonic cleaning with city tap water. When the preliminary cleaning with city tap water is completed, the control valve 39 is closed and, at the same time, a control valve 13 is opened to drain city tap water in the cleaning-sterilizing bath 26. Then, a predetermined amount of saline solution in the saline solution tank 17 is supplied by a pump 18 to each of the alkaline-water-producing bath 2 and the acidic-water-producing bath 3 of the water-flow type electrolysis bath 29. At the same time, the cathode 7 and the anode 8 of the electrolysis bath 29 are applied with electric current from an electrolysis power supply 25 to electrolyze the saline solution, and alkaline water generated is directly supplied to the cleaning-sterilizing bath 26 through a water-feeding pipe to clean the endoscopic camera instrument with the alkaline water. The cleaning is carried out continuously for a predetermined time while the ultrasonic generator 5 is being actuated. When the ultrasonic cleaning with alkaline water is completed, supply of saline solution is stopped, the electrolysis is stopped, and the alkaline water in the cleaning-sterilizing bath is drained. Then, it is preferred that city tap water is supplied to conduct rinsing in the same manner as the preliminary cleaning. The acidic water generated in the acidic-water-producing bath 3 during the ultrasonic cleaning with alkaline water, is stored in the acidic water tank 30.

Then, a pump 18' is started to supply continuously or intermittently acidic water in the acidic water tank 30 to the cleaning-sterilizing bath 26 through the alkaline-water-producing bath 2 of the water-flow type electrolysis bath 29, to conduct a sterilizing treatment for the endoscopic camera instrument that has been subjected to the ultrasonic cleaning with alkaline water. After the sterilizing treatment, the control valve 13 is opened to drain the acidic water in the cleaning-sterilizing bath. In this example, the endoscopic camera instrument that has been subjected to the sterilizing treatment, is subjected to ultrasonic cleaning with city tap water to completely rinse out e.g. acidic water adhered to the surface of the endoscopic camera instrument, and finally, the instrument is dried by a warm-air apparatus 15.

In the water-flow type electrolysis bath of this example, alkaline water and acidic water may be produced with higher concentrations than those to be used for cleaning and sterilizing, by electrolysis, and they may be diluted to predetermined concentrations when they are supplied to the cleaning-sterilizing bath 26. The ratio of the dilution is preferably about 2 to 5 times. If the dilution ratio is lower than this, there is no merit of the small space. On the contrary, if the dilution ratio is high, not only the stability of acidic water is deteriorated, but also the oxidation power of the acidic water becomes strong and selection range of materials constituting water-flow portions becomes narrower, which increases cost, such being not preferred.

Such a method of producing electrolyzed water having high concentration and diluting it for use, is suitable for a batch type cleaning in which electrolyzed water is produced for e.g. every cleaning. In the above-mentioned water-flow type method of FIG. 3, acidic water from the acidic-water-producing bath 3 is once stored in the acidic water tank 30, and supplied to the cleaning-sterilizing bath 26 through the alkaline-water-producing bath 2. However, in this batch type method, electrolyzed water having high concentration produced in the electrolysis bath is sequentially diluted and used, whereby the acidic water from the acidic-water-producing bath 3 can be used without storage in the acidic water tank 30. Namely, in FIG. 3, alkaline water in the alkaline-water-producing bath 2 is diluted with city tap water and supplied to the cleaning-sterilizing bath 26 to conduct cleaning. Thereafter, acidic water in the acidic-water-producing bath 3 is moved directly to the alkaline-water-producing bath 2 without storage in the acidic water tank 30, and the alkaline water is diluted with city tap water to have a desired concentration to be supplied to the cleaning-sterilizing bath 26 for sterilization. Here, this batch-type method has a merit that the acidic water tank 30 can be omitted. However, in order to obtain a predetermined amount of electrolyzed water, the capacity of water-flow type electrolysis bath is preferably larger than that of the water-flow type bath of FIG. 3.

According to the method of this example, since acidic water is supplied to the cleaning-sterilizing bath 26 through the alkaline-water-producing bath 2 of the electrolysis bath, it is possible to dissolve and remove, with the acidic water, precipitated product composed mainly of e.g. calcium generated and adhered to the cathode, the separating membrane, the inner surface of the electrolysis bath or the water-flow passage at a time of electrolysis. The precipitated product adhered to the surface of the electrode would increase resistance against electrolysis current, the precipitated product adhered to the separating membrane would prevent movement of ions to decrease electrolysis efficiency. Further, the precipitated product adhered to the water-flow passage would increase resistance against water flow, and change the balance of water flowing through the electrolysis bath, whereby electrolysis may not result in the way as it is set up.

Therefore, heretofore, in order to prevent such adhesion and deposition of precipitated products, it has been conducted e.g. removal of calcium or magnesium in water by employing e.g. ion-exchange resin, or so-called reverse cleaning in which the polarities of the electric current applied to the electrodes, are switched at every predetermined time of electrolysis treatment or every predetermined amount of treatment water amount, to dissolve and remove precipitated products. However, such a switching of electrodes causes repeated oxidation→reduction→oxidation (or reverse) of the surface of the electrodes, which accelerates dissolution and wearing of electrodes even in a case of insoluble electrodes made of e.g. platinum, and reduces the lifetime of electrodes. Further, since not only the quality of water is different depending on the place of use, but also the adhesion amount changes seasonally, the optimum setting of switching polarities is extremely difficult.

Further, there is a method of employing a polarity selection membrane for the separating membrane to prevent cations from moving from the acidic-water-producing bath to the alkaline-water-producing bath, to reduce precipitated product. However, polarity selection membranes are expensive, and most of them are wet-type membranes which are not easily produced and require troublesome maintenance so that such a membrane is not dried and does not have bacteria or mold when the electrolysis bath is not used. Further, if the electrolysis performance is decreased due to effect of the precipitated products, it becomes necessary to clean the electrolysis bath and the water-flow passage with an acid such as dilute hydrochloric acid to remove such precipitated products, and such a removing work needs to be committed to a specialist for maintenance. On the other hand, in this example, since the precipitated products are dissolved and removed with acidic water at every time of use, such maintenance is not necessary.

Further, in a case of using an electricity-flow type electrolysis bath, acidic water is not affected by ultrasonic waves applied at a time of alkaline-water cleaning, and dissipates no residual gas, whereby there is a merit that the sterilizing ability of the acidic water tends to be maintained.

Cleaning and sterilization of a hard-type endoscope of the present invention has been described. However, the present invention may also be applied to a soft type endoscope by adding a member for cleaning inside of the conduit of a soft type endoscope in the same manner as a known-cleaning apparatus. Further, it is possible to clean and sterilize e.g. operation tools other than endoscopes or implants.

INDUSTRIAL APPLICABILITY

According to the present invention, e.g. an endoscopic camera instrument is at least ultrasonic-cleaned with alkaline water produced by electrolysis, and the cleaning is conducted in an alkaline-water-producing bath of the electrolysis bath or in a cleaning bath communicated with the alkaline-water-producing bath, to remove e.g. lipid or solid protein adhered to the endoscopic camera instrument etc., and then, the alkaline water is replaced by acidic water obtained by electrolysis to sterilize and clean the endoscopic camera instrument etc., whereby the cleaning apparatus can be small-sized as compared with a conventional apparatus in which an electrolysis apparatus and a cleaning bath are provided separately. By such a construction, it is easy to move the apparatus and it is possible to bring the apparatus to the use site for use. Further, it is possible to clean and sterilize an endoscopic camera instrument etc. without moving the instrument from bath to bath between cleaning and sterilizing treatments. Particularly, since a hard type endoscope can be cleaned as a main body of the endoscope is connected with a camera, its practical effect is significant.

Further, since after the cleaning with alkaline water, acidic water is moved to the alkaline-water-producing bath to carry out sterilization, or the acidic water is supplied to the cleaning bath through the alkaline-water-producing bath to carry out sterilization, layers of calcium or magnesium contained in city tap water and precipitated on electrodes of the alkaline-water-producing bath or on the portion of the bath in contact with water level at the time of producing alkaline water, can be dissolved and removed with the acidic water, whereby conventional maintenances such as switching of polarities of electrolysis current or cleaning with acid, become unnecessary.

Further, prior to the sterilization with acidic water, ultrasonic cleaning with alkaline water is conducted to remove organic matter preventing oxidation-sterilization power of the acidic water such as blood or fat or human body, whereby the effects of killing bacteria and virus of acidic water can be effectively exhibited. In particular, by combining water-ultrasonic cleaning with alkaline water as preliminary cleaning, with ultrasonic cleaning with alkaline water, the above-mentioned dirt adhered to an endoscopic camera instrument etc. can be completely removed.

Thus, dirt adhered to an endoscopic camera instrument etc. is sufficiently removed and sterilization is carried out, whereby it is possible to prevent generation of e.g. bacteria or mold taking organic matter remained on the surface of the instrument after sterilization as nutrition source. Further, even, e.g., a prion which is not removable by insufficient cleaning and heating-sterilization, can be removed.

Further, after sterilization with acidic water is completed, city tap water is supplied to the cleaning-sterilizing bath to wash out acidic water adhered to the endoscopic camera instrument etc., bacteria killed or dissolved by the acidic water, product formed from dirt, and acidic water adhering and remaining in the bath, whereby corrosion, rust or deterioration of the endoscopic camera instrument etc. can be suppressed to be within a range that they are not problem for practical use. Further, by removing decomposed product of bacteria or dirt from the surface of the endoscopic camera instrument etc. at the same time, adhesion or growth of bacteria on the surface of the instrument after sterilization can be prevented. In particular, by conducting ultrasonic cleaning for the water cleaning, its effect is increased.

The present invention is based on Japanese Patent Application No. 2003-143651 (filed on May 21, 2003), and its entirety is hereby included by reference.

The invention claimed is:

1. A method for cleaning and sterilizing an endoscopic camera instrument, comprising the steps of:
    producing alkaline water and acidic water in respective cathode and anode chambers of an electrolysis bath by electrolysis;
    conducting ultrasonic cleaning of the endoscopic camera instrument in the cathode chamber of the electrolysis bath with the alkaline water produced by the electrolysis, to remove lipid and solid protein adhering to the endoscopic camera instrument;
    subsequently transferring the acidic water produced by the electrolysis into the cathode chamber of the electrolysis bath; and
    cleaning and sterilizing the endoscopic camera instrument in the cathode chamber of the electrolysis bath with the acidic water.

2. The method according to claim 1, further comprising:
    conducting preliminary cleaning of the endoscopic camera instrument with water;
    subsequently cleaning and sterilizing the endoscopic camera instrument with the acidic water produced by the electrolysis; and
    conducting cleaning of the endoscopic camera instrument with water.

3. The method according to claim 1 or 2, wherein the electrolysis bath has electrodes in the cathode and anode chambers, which are partitioned by a membrane;
    the method comprising:
    conducting preliminary cleaning of the endoscopic camera instrument inserted into the cleaning bath by ultrasonic cleaning with water;
    performing said step of conducting ultrasonic cleaning by conducting ultrasonic cleaning of the endoscopic camera instrument in the cathode chamber with the alkaline water produced by electrolysis of the saline solution supplied to the electrolysis bath;
    subsequently draining the alkaline water from the cathode chamber and supplying acidic water stored in an acidic-water-producing bath into the cathode chamber;
    performing said step of cleaning and sterilizing by sterilizing and cleaning the endoscopic camera instrument in the cathode chamber with the acidic water; and
    further conducting cleaning of the endoscopic camera instrument with water.

4. The method according to claim 1 or 2, the electrolysis bath further comprising a water storage tank connected to the anode chamber via a first water-feeding pipe, comprising the steps of:
    supplying the acidic water to the water storage tank via the first water-feeding pipe, and
    supplying the acidic water stored in the storage tank to the cathode chamber so as to conduct sterilization.

5. The method according to claim 1, further comprising rinsing and cleaning the endoscopic camera instrument subjected to the ultrasonic cleaning with alkaline water with water before sterilizing and cleaning the endoscopic camera instrument with the acidic water.

6. The method according to claim 1, further comprising automatically controlling operations from preliminary cleaning with water to at least the sterilization and cleaning with the acidic water.

7. The method according to claim 1, the endoscopic camera instrument further comprising an endoscope attached with a camera.

* * * * *